United States Patent [19]

Grosse et al.

[11] Patent Number: 4,473,509

[45] Date of Patent: Sep. 25, 1984

[54] PROCESS FOR MAKING PHOSPHONIC ANHYDRIDES

[75] Inventors: Jürgen Grosse, Hürth; Werner Pieper, Erftstadt, both of Fed. Rep. of Germany

[73] Assignee: Hoechst Aktiengesellschaft, Fed. Rep. of Germany

[21] Appl. No.: 442,103

[22] Filed: Nov. 16, 1982

[30] Foreign Application Priority Data

Dec. 10, 1981 [DE] Fed. Rep. of Germany ....... 3148881

[51] Int. Cl.$^3$ .............................................. C07F 9/28
[52] U.S. Cl. .................................. 260/545 P; 260/988
[58] Field of Search ..................... 260/545 P, 985, 988

[56] References Cited

U.S. PATENT DOCUMENTS 4,101,573 7/1978 Gehrmann et al. ............. 260/543 P
4,267,125 5/1981 Duersch et al. ................. 260/545 P

OTHER PUBLICATIONS

Houben-Weyl, *Methoden der organischen Chemie*, 4th Edition, vol. XII/1, (1963), p. 612.
Grasse, Juergen et al., Angew. Chem., (1982), vol. 94, No. 7, p. 560.
Currell, Brian R. et al., The British Polymer Journal, Sep. 1981, pp. 122-125.

*Primary Examiner*—Natalie Trousof
*Assistant Examiner*—L. Hendriksen
*Attorney, Agent, or Firm*—Connolly and Hutz

[57] ABSTRACT

The disclosure relates to a process for making phosphonic anhydrides of general formula (I)

$$(RPO_2)_n \cdot H_2O \qquad (I)$$

in which R stands for an alkyl or aryl radical having from 1 to 6 carbon atoms and n stands for a value between 2 and 20. To this end, the disclosure provides for a compound of general formula (II)

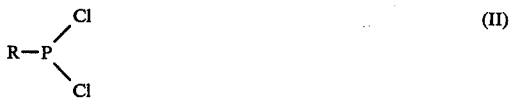

in which R has the meaning given above to be oxidized with concentrated sulfuric acid under inert gas and in the presence of a diluent at a temperature between 0° and 100° C., the compound of general formula (II) and sulfuric acid being used in a molar ratio of about 1:1.

8 Claims, No Drawings

PROCESS FOR MAKING PHOSPHONIC ANHYDRIDES

The present invention relates to a process for making phosphonic anhydrides by subjecting alkyl or aryldichlorophosphanes to oxidation.

Three basic methods for making phosphonic anhydrides were described heretofore in the literature, which more particularly provide:

(1) for two phosphonic acid derivatives to be subjected to condensation;
(2) for anhydride functions to be conferred upon phosphonic acid derivatives with the aid of organic compounds; and
(3) for phosphonous acids to be subjected to oxidation and condensation to cause anhydride formation.

The first of these methods comprises reactions such as those described by K. Sasse in Houben-Weyl, Methoden der organischen Chemie, 12/1, 612–613 (1963), Georg Thieme Verlag, Stuttgart, namely (a) the condensation of equimolar mixtures of phosphonous acids and their dichlorides in accordance with the following equation:

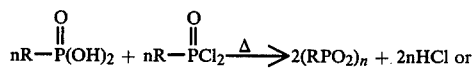

(b) the thermal decomposition of phosphonic acid ester chlorides in accordance with the following equation:

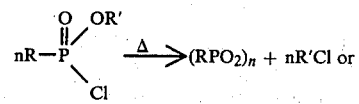

(c) the dismutation of pyrophosphonic acid esters in accordance with the following equation:

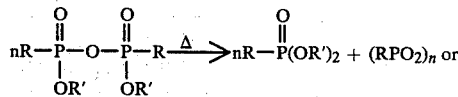

(d) the thermal dehydration of phosphonic acids at temperatures of 250°–450° C. under reduced pressure in accordance with the following equation:

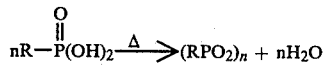

In order to effect the reaction of equation (a), it is necessary for two compounds of the phosphonic acid group to be first synthesized, whereas the reactions of equations (b) and (c) use difficultly obtainable intermediate products as feed material which therefore are of little commercial interest as is the energetically unfavorable reaction of equation (d).

The methods referred to under (2) above for making phosphonic acid anhydrides include the reaction of phosphonic acid dichlorides with carboxylic anhydrides at elevated temperatures (disclosed in DE-PS No. 2 908 264), and also the reaction of phosphonic acid chlorides with paraformaldehyde disclosed by K. Moedritzer in J. Amer. Chem. Soc. 83 (4381) (1961). These two reactions can be illustrated by the following two reactions equations:

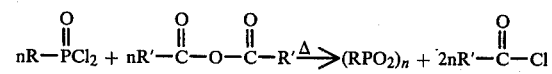

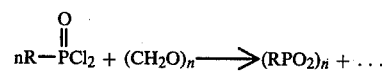

The first of these two processes has the disadvantage of requiring long reaction periods whilst the second yields dark-colored products in poor yields.

The methods referred to under (3) above for making phosphonic anhydrides include processes which are based on the oxidation of phosphonous acids with the use of sulfur or sulfuryl chloride as oxidant. These processes were disclosed by E. E. Nifant'ev et al. in J. Gen. Chem. USSR 50, 2159 (1980) and J. Gen. Chem. USSR 49, 1678 (1979). Sulfur, however, is an oxidant which is not very suitable for oxidizing phosphonous acids as the reaction occurs at elevated temperature only with molten sulfur.

The present invention now provides a process which obviates the adverse effects associated with these prior methods.

The present invention relates more particularly to a process for making phosphonic anhydrides of general formula (I)

$$(RPO_2)_n \cdot H_2O \qquad (I)$$

in which R stands for an alkyl or aryl radical having from 1 to 6 carbon atoms and n stands for a value between 2 and 20, which comprises: oxidizing a compound of general formula (II)

in which R has the meaning given above, with concentrated sulfuric acid under inert gas and in the presence of a diluent at a temperature between 0° and 100° C. with escape of hydrogen chloride and sulfur dioxide, the compound of general formula (II) and sulfuric acid being used in a molar ratio of about 1:1, terminating the reaction and separating the diluent from the product of general formula (I).

Preferred features of the present invention provide for the parameter n to stand for a value between 2 and 16 and for the compound of general formula (II) and sulfuric acid to be used in a molar ratio of 1–1.2:1.

The preferred diluents are ethers which are used for their susceptibility of forming adducts with mineral acids. Ethers boiling at a temperature within the range about 30° to 140° C., such as diethylether, diisopropylether, dibutylether or dioxane, are more particularly used as diluents.

The mean chain length n of the phosphonic anhydride can be acted upon by the introduction of minor proportions of water into the reaction bath, the water being contained e.g. in sulfuric acid containing less than 100% $H_2SO_4$ or in a hydrous diluent.

The reaction in accordance with this invention takes an exothermal course so that it is good practice for the reaction mixture to be cooled, if desired, so as to ensure that the reaction takes place at low temperature.

The product of general formula (II) used as feed material in the present process is a readily obtainable commercial product.

The following statements are intended further to illustrate the process of this invention.

In carrying out the process, anhydrous sulfuric acid, which can be obtained from 98% sulfuric acid and oleum, and the compound of general formula (II) are successively introduced dropwise with agitation and while cooling, if desired, into the solvent. Upon the dropwise introduction of the compound of formula (II), the exothermal reaction commences at once, stoichiometric proportions of $SO_2$ and HCl being split off, which are extensively removed from the reaction chamber and can be neutralized by scrubbing with water or sodium hydroxide solution. The sequential order of adding the components can naturally be inversed. Among all reactants, the product of general formula (I) is the only compound which is sparingly soluble in the diluent used, and which therefore deposits as a lower phase easy to separate. Residual solvent and reaction gases which may be found to adhere to the final product can extensively be removed therefrom by stripping under vacuum.

The phosphonic anhydrides can be separated quantitatively.

Unlike the processes described heretofore, the present process is an easy-to-carry out and energetically favorable process in which the feed materials are selected from commercially interesting readily accessible products. A further beneficial effect of the present process resides in the fact that the reaction occurs spontaneously and that the by-products are all gaseous and therefore easy to separate. Still further, the desired final product is sparingly soluble in the diluent so that it can readily be separated and isolated therefrom.

The phosphonic anhydrides obtained by the process of this invention are valuable intermediates for use in the production of preparation agents for textile fibers, flame-retarding agents or condensation agents for use in synthesizing peptides or amides.

The following Examples illustrate the invention.

EXAMPLE 1

150 ml dry diethylether was placed in a 250 ml multi-necked flask provided with an agitator, thermometer, reflux condenser, dropping funnel and gas inlet tube, and 35.5 g (0.36 mol) sulfuric acid of about 100% strength was added dropwise under nitrogen within 30 minutes while cooling with ice water. A colorless clear solution which was admixed dropwise within 1 hour with 44.2 g (0.38 mol) dichloromethylphosphane was obtained. The boiling ether did not permit the reaction temperature to exceed a given maximum. Hydrogen chloride and sulfur dioxide which issued from the reaction chamber were removed from the stream of inert gas by scrubbing with water or sodium hydroxide solution. The final product deposited as a lower phase. Solvent or diluent were removed by decantation and the final product was freed from adhering ether and reaction gas under high vacuum. 29.7 g white solid material was obtained. Spectroscopic data and the 1:4 ratio of methanephosphonic acid to methanephosphonic acid monomethylester determined by subjecting the product to methanolysis indicated a mean chain length n=5 for the product. The yield was 0.07 mol, corresponding to 100% of the theoretical.

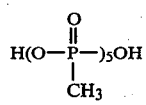

EXAMPLE 2

In an apparatus as described in Example 1, 110 g (1.1 mol) 100% sulfuric acid was dissolved in 450 ml dried diethylether while cooling with ice water. The ether solution was heated to boiling and admixed dropwise with 161 g (1.2 mol) dichloroethylphosphane; hydrogen chloride and sulfur dioxide issued from the reaction chamber. Next, the solvent and residual gaseous reaction products were expelled under vacuum at 50°-60° C. bath temperature. 104.4 g residue was obtained. Spectroscopic data and the 1:15 ratio of ethanephosphonic acid to ethanephosphonic acid monomethylester determined by subjecting the product to methanolysis indicated a mean chain length n=16 for the product. The yield was 0.07 mol, corresponding to 100% of the theoretical.

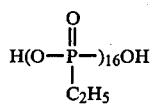

EXAMPLE 3

In an apparatus as described in Example 1, 27 g (0.27 mol) about 100% sulfuric acid in 80 ml moist dibutylether was added dropwise while cooling with water so that the temperature of the mixture did not exceed 25° C. 49.5 g (0.25 mol) dichlorophenylphosphane was introduced dropwise into the solution so that the reaction temperature did not exceed 80° C. Resulting hydrogen chloride and sulfur dioxide were removed from the issuing stream of inert gas in successive scrubbing stages. The reaction mixture formed two phases of which the upper ether phase was separated. The residue was freed under vacuum from residual solvent and dissolved gaseous reaction products. Phenylphosphonic anhydride was obtained in the form of a viscous slightly yellowish oil in quantitative yield. The anhydride had a mean chain length n=2.5.

EXAMPLE 4

In an apparatus as described in Example 1, a solution of 50.4 g (0.51 mol) about 100% $H_2SO_4$ in 200 ml dried diethylether was admixed dropwise with 92 g (0.51 mol) dichlorophenylphosphane so that the solvent boiled under reflux. $SO_2$ and HCl which issued were removed from the stream of inert gas by scrubbing treatment. The product was freed under vacuum from solvent and dissolved gaseous reaction products and separated in the form of a slightly yellowish viscous oil. The phenylphosphonic anhydride had a mean chain length n=7 and was obtained in a yield of 78 g (0.078 mol), corresponding to 100% of the theoretical.

We claim:

1. Process for making phosphonic anhydrides of formula (I)

$(RPO_2)_n \cdot H_2O$ in which R stands for an alkyl or aryl radical having from 1 to 6 carbon atoms and n stands for a value between 2 and 20, which comprises: oxidizing a compound of formula (II)

in which R has the meaning given above, with concentrated sulfuric acid under inert gas and in the presence of a diluent at a temperature between 0° and 100° C. with escape of hydrogen chloride and sulfur dioxide, the compound of formula (II) and sulfuric acid being used in a molar ratio of about 1:1, terminating the reaction and separating the diluent from the product of formula (I).

2. A process for making phosphonic anhydrides of formula (I)

$(RPO_2)_n \cdot H_2O$ in which R stands for an alkyl or aryl radical having from 1 to 6 carbon atoms and n stands for a mean chain length of from 2 to 20, which comprises: oxidizing a compound of formula (II)

in which R has the meaning given above, with about 100% sulfuric acid in a molar ratio of (1 to 1.2):1 under inert gas and in the presence of a diluent at a temperature between 0° and 100° C. with escape of hydrogen chloride and sulfur dioxide, and with formation, after terminating the reaction, of an upper phase and a lower phase, separating the lower phase and removing adhering residual solvent and reaction gases therefrom by stripping under vacuum.

3. The process as claimed in claim 2, wherein the parameter n stands for a value between 2 and 16.

4. The process as claimed in claim 1, wherein the diluent is an ether having a boiling point of about 30° to 140° C.

5. The process as claimed in claim 4, wherein the diluent is diethylether, diisopropylether, dibutylether or dioxane.

6. The process as claimed in claim 2, wherein the mean chain length of the compound of formula (I) is lowered by the introduction of minor proportions of water into the reaction batch.

7. The process as claimed in claim 6, wherein the water is introduced by using sulfuric acid containing less than 100% $H_2SO_4$.

8. The process as claimed in claim 6, wherein the water is introduced by using a hydrous diluent.

* * * * *